(12) United States Patent
Sauska et al.

(10) Patent No.: US 6,875,988 B1
(45) Date of Patent: Apr. 5, 2005

(54) GERMICIDAL LAMP AND PURIFICATION SYSTEM HAVING TURBULENT FLOW

(75) Inventors: Christian Sauska, Orange, CT (US); Arpad Pirovic, Woodbridge, CT (US)

(73) Assignee: Light Sources, Inc., Orange, CT (US)

( * ) Notice: Subject to any disclaimer, the term of this patent is extended or adjusted under 35 U.S.C. 154(b) by 48 days.

(21) Appl. No.: 10/051,705

(22) Filed: Jan. 17, 2002

(51) Int. Cl.[7] .............................. H01J 5/50; C02F 1/32
(52) U.S. Cl. ................. 250/455.11; 250/438; 250/436; 96/224; 422/24; 422/186.3
(58) Field of Search ............................. 250/455.11, 438, 250/436, 365, 504 R; 96/224; 422/24, 186.3

(56) References Cited

U.S. PATENT DOCUMENTS

| | | | |
|---|---|---|---|
| 3,560,786 A | | 2/1971 | Shurgan |
| 3,791,790 A | * | 2/1974 | Wyndham et al. .......... 210/251 |
| 3,988,633 A | | 10/1976 | Shurgan et al. |
| 5,069,885 A | | 12/1991 | Ritchie |
| 5,116,582 A | | 5/1992 | Cooper et al. |
| 5,230,792 A | | 7/1993 | Sauska et al. |
| 5,422,487 A | | 6/1995 | Sauska et al. |
| 5,498,924 A | | 3/1996 | Northrop |
| 5,785,845 A | * | 7/1998 | Colaiano ..................... 210/167 |
| 5,833,740 A | * | 11/1998 | Brais ............................... 96/16 |
| 6,053,968 A | * | 4/2000 | Miller ........................ 96/224 |

FOREIGN PATENT DOCUMENTS

| | | |
|---|---|---|
| EP | 0 202 820 | 11/1986 |
| FR | 80 549 | 5/1963 |
| WO | WO 01/37675 A2 | 5/2001 |

* cited by examiner

*Primary Examiner*—John R. Lee
*Assistant Examiner*—James J. Leybourne
(74) *Attorney, Agent, or Firm*—Fattibene & Fattibene; Paul A. Fattibene; Arthur T. Fattibene

(57) ABSTRACT

A germicidal lamp having a non-uniform contour increasing turbulence. An ultraviolet fluorescent lamp used in a purification system having a helical groove increasing turbulence of the fluid flow. The non-uniform contour may be placed directly on the tubular envelope forming the lamp or may be formed on a separate envelope enclosing a conventional cylindrical tubular germicidal lamp. The germicidal lamp having a non-uniform contour when placed in a fluid flow, such as water or air, creates turbulence, which improves the efficiency of the germicidal action. Smaller, more efficient purification systems requiring less exposure time are obtained.

14 Claims, 3 Drawing Sheets

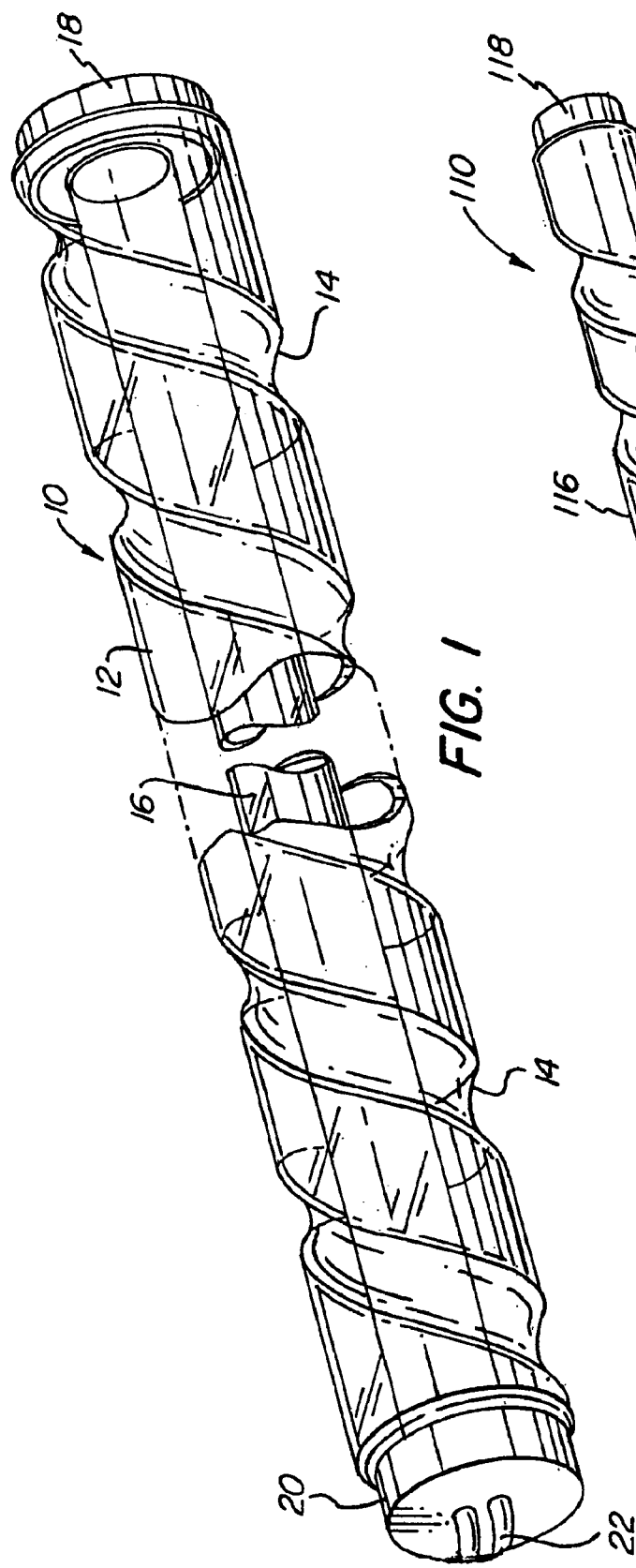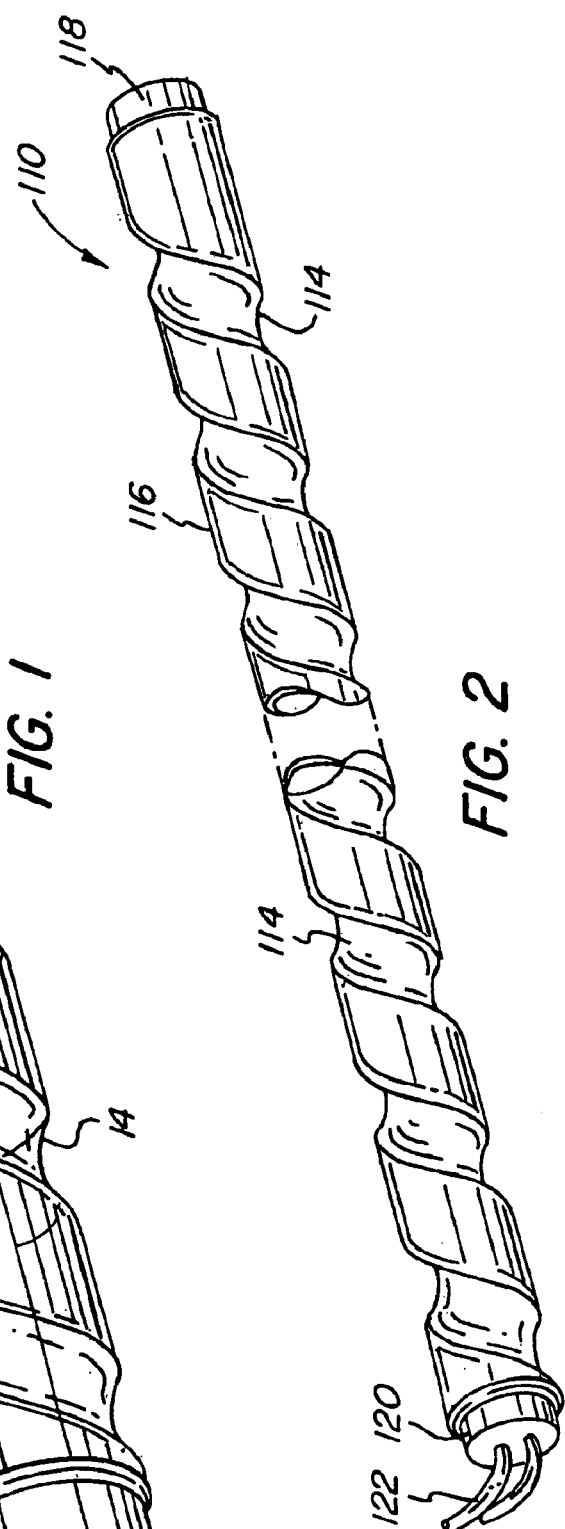

GERMICIDAL LAMP AND PURIFICATION SYSTEM HAVING TURBULENT FLOW

FIELD OF TEE INVENTION

The present invention relates in general to a germicidal lamp and purification system, and more particularly to a germicidal lamp creating a turbulent flow.

BACKGROUND OF THE INVENTION

Ultraviolet lamps are often used in water purification systems. The ultraviolet or germicidal lamps are used to treat wastewater. Tubular germicidal lamps are often placed in a flow chamber, typically parallel with the direction of fluid flow. One such lamp is disclosed in U.S. Pat. No. 5,422,487 entitled "Waste Water Purification System With Complementary Interlocking Germicidal Lamp and Socket Construction" issuing to Sauska et al on Jun. 6, 1995, which is herein incorporated by reference. Therein disclosed is a waste water treating apparatus for disinfecting a liquid affluent. Germicidal or ultraviolet lamps are disposed within the flow of the affluent or waste water to be treated. The lamps are longitudinally disposed throughout the parallel flow relationship to the waste water flowing there around.

In other water purification systems, the water being treated is kept apart from contacting the germicidal lamp by placement next to independent fluid conduits. Those systems are generally more costly due to the more complicated structure. One such system is disclosed in U.S. Pat. No. 5,230,792 entitled "Ultraviolet Water Purification System With Variable Intensity Control", issuing to Sauska et al on Jul. 27, 1993, which is herein incorporated by reference.

While these prior water purification systems are generally adequate, they usually require fairly long lengths of water flow. Additionally, while the water adjacent to the germicidal lamp is often treated adequately, however, the water flowing at a greater distance from the germicidal lamp may require additional exposure or treatment time. As a result, the overall exposure time is often increased to assure that the water more distant from the lamp is adequately treated.

Therefore, there is a need to improve the purification and treatment of a fluid with germicidal lamps. Additionally, there is a need to reduce the overall size of the purification or germicidal system using germicidal lamps, and to reduce the required time of exposure and the thoroughness or evenness of the germicidal effect.

SUMMARY OF THE INVENTION

The present invention is a germicidal lamp used in a purification or germicidal system that increases the turbulence of the fluid flow which improves the germicidal action. A tubular ultraviolet or germicidal lamp has an exterior non-uniform contour for increasing fluid turbulence. In one embodiment, the non-uniform contour is a helical groove along the length of the tubular germicidal lamp. In another embodiment, the non-uniform contour is a double helical groove along the length of the germicidal lamp. The tubular germicidal lamps are placed within the fluid flow, increasing turbulence. This improves the effectiveness of the germicidal lamp. The tubular lamps may be placed parallel to the direction of flow or transverse to the direction of flow. In another embodiment of the present invention, the germicidal lamp having a non-uniform contour is used to provide a germicidal action in a room. Airflow over the non-uniform contour of the germicidal lamp creates turbulence, which enhances the germicidal effect of the germicidal lamp and purifies the air.

Accordingly, it is an object of the present invention to improve the purification or germicidal treatment of a fluid.

It is an advantage of the present invention that increased turbulence is achieved that improves the efficiency of the germicidal lamp.

It is a feature of the present invention that a germicidal lamp has a non-uniform contour that creates turbulent flow.

These and other objects, advantages, and features will become readily apparent in view of the following more detailed description.

IN THE DRAWINGS

FIG. 1 is a perspective view in partial section illustrating an embodiment of the present invention.

FIG. 2 is a perspective view of another embodiment of the present invention.

DETAILED DESCRIPTION OF THE PREFERRED EMBODIMENTS

Figure 3:
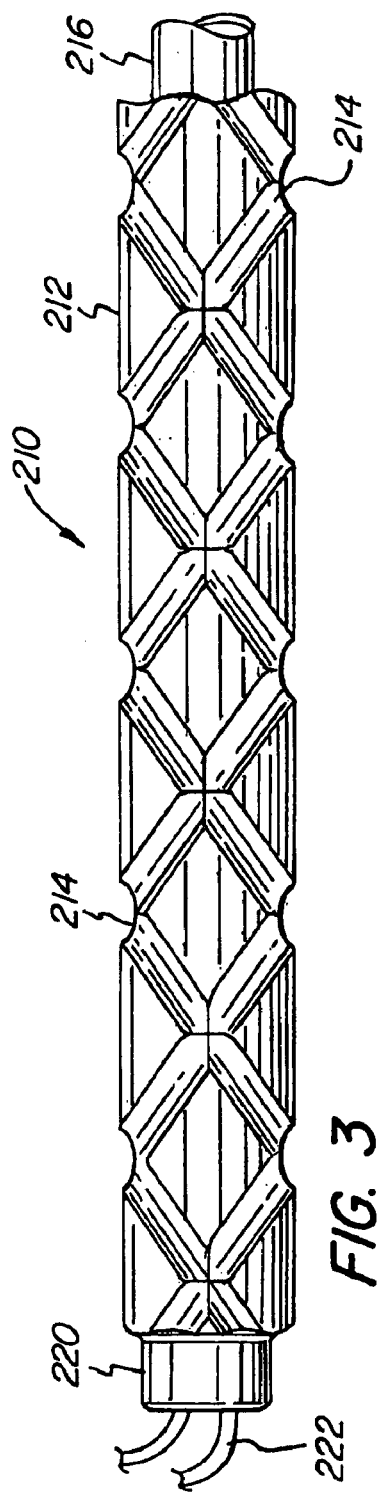
FIG. 3 is a front elevational view of another embodiment of the present invention.

FIG. 1 is a perspective view in partial section of a germicidal lamp 10 of the present invention. The germicidal lamp 10 comprises a transparent tubular envelope 12. The tubular envelope 12 has a non-uniform contour or helical groove 14. The tubular envelope 12 is sealed by end caps 18 and 20. Extending through end cap 20 are connectors 22. Contained within the envelope 12 is an ultraviolet lamp 16. The envelope 12 is used to protect the ultraviolet lamp 16. The helical groove 14 may be formed in the envelope by any conventional technique. For example, the techniques disclosed in U.S. Pat. No. 3,968,633 entitled "Fluorescent Lamp With Envelope Groove" issuing to Shurgan et al on Oct. 26, 1976, which is herein incorporated by reference. Therein disclosed is a method and apparatus for making grooves in a fluorescent lamp using a plurality of heat sources. Other shaped grooves may be utilized in the present invention provided the grooves provide sufficient turbulence when placed in a fluid flow.

FIG. 2 is a perspective view illustrating another embodiment of the present invention. The germicidal lamp 110 is formed from an ultraviolet lamp 116 with the helical groove 114 formed directly therein. End caps 118 and 120 seal the lamp 116. Electrical contacts 122 extend from end cap 120. The ultraviolet lamp 116 is preferably a fluorescent lamp that produces ultraviolet radiation.

FIG. 3 is a side elevational view of another embodiment of the present invention. The germicidal lamp 210 has an envelope 212 having a plurality of helical grooves 214 formed therein. The helical grooves 214 cross forming a double helix. Placed within the envelope 212 is an ultraviolet lamp 216. Connector 222 extends from the cap 220 for powering the ultraviolet lamp 216.

Figure 4:
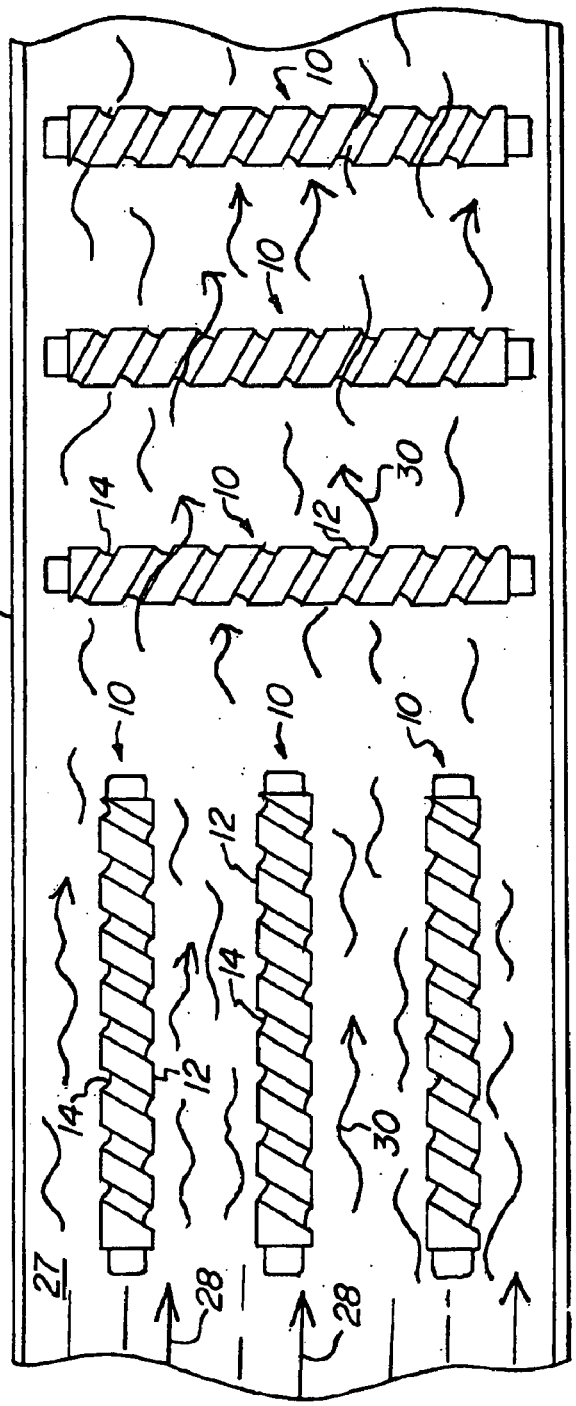
FIG. 4 is a plan view of a water purification system embodiment of the present invention.

FIG. 4 is a plan view of a water purification system 24 according to the present invention. A chamber 26 has a fluid 27 flowing therein in the direction of arrows 28. Initially, the fluid flow is laminar. A plurality of germicidal lamps 10 is placed within the fluid flow 28. The germicidal lamp 10 may be placed having the longitudinal axis substantially parallel to the fluid flow, represented by arrow 28, or transverse to the flow direction. The helical grooves formed in the envelope 12 create a non-uniform contour that generates or creates turbulence in the fluid flow represented by arrows 30. This turbulence in the fluid flow breaks up the laminar flow, represented by arrows 28, and improves the efficiency of the purification system. The turbulence makes possible the more even exposure of the ultraviolet radiation within the volume of fluid. This permits more efficient exposure, which reduces the size of the water purification system as well as the time of exposure required to purify the water.

While FIG. 4 illustrates the application of the germicidal lamp 10 illustrated in FIG. 1, it should be appreciated that any germicidal lamp having a non-uniform contour may be utilized so as to increase turbulence in the fluid flow. The germicidal lamp 110 illustrated in FIG. 2 and the germicidal lamp 210 illustrated in FIG. 3 may be utilized in the water purification system illustrated in FIG. 4. When the germicidal lamp 110 illustrated in FIG. 2 is used, an additional advantage may be obtained in that increased light output may be created. However, the fabrication of the germicidal lamp 110, as illustrated in FIG. 2, may be more costly.

Figure 5:
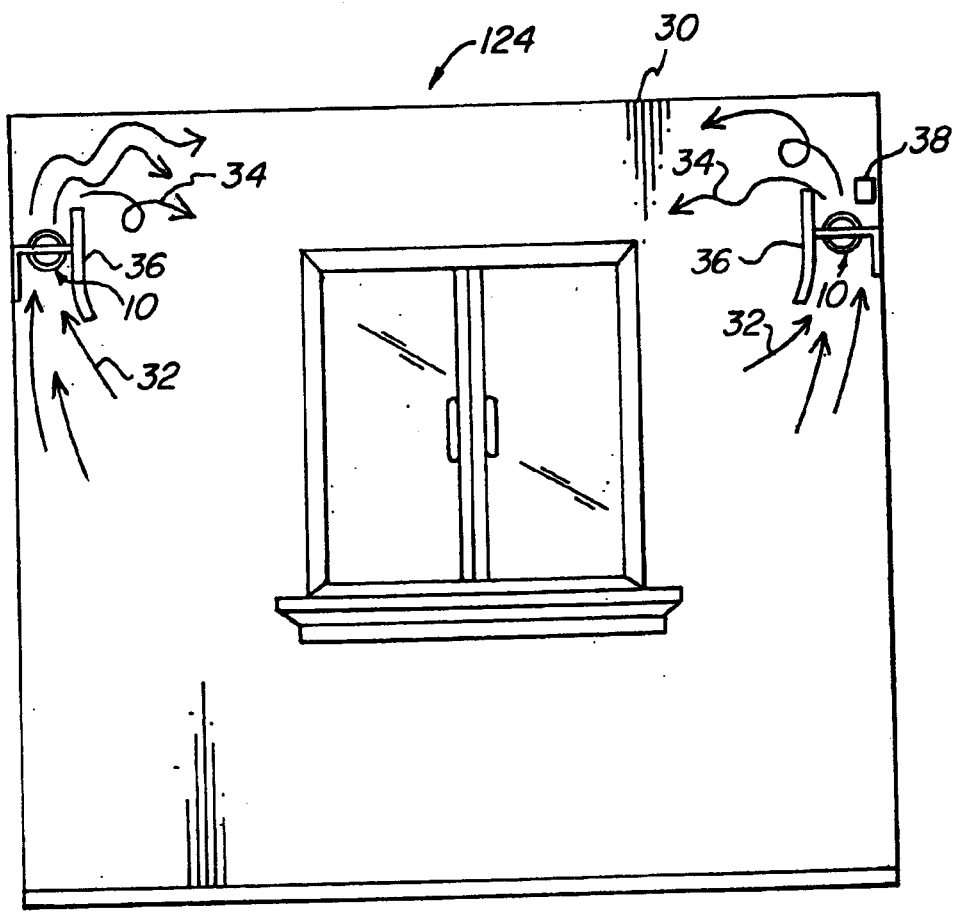
FIG. 5 is a side elevational view of an air purification system of an embodiment of the present invention.
Figure 6:
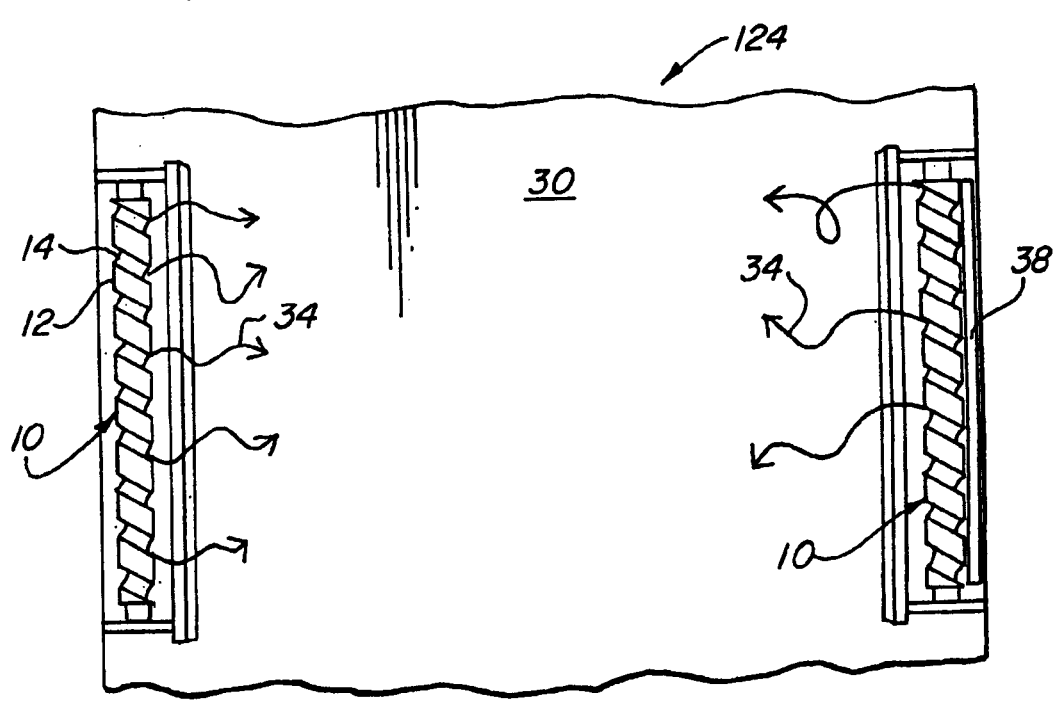
FIG. 6 is a planview of the embodiment illustrated in FIG. 5.

FIGS. 5 and 6 illustrate an air purification system within a room 30. Germicidal lamps 10 are placed near the ceiling of the room 30. Arrows 32 represent airflow adjacent a wall of the room 30. Arrows 34 represents the turbulent airflow after passing over the germicidal lamp 10. A fan or blower 38 may augment the airflow. The germicidal lamp 10 has a non-uniform contour formed by the envelope 12 and the helical grooves 14. In the air purification system illustrated in FIGS. 5 and 6 of this embodiment, it may be preferable to utilize a germicidal lamp 110 as illustrated in FIG. 2 without a separate cover or envelope.

In the air purification embodiment illustrated in FIGS. 5 and 6, air may be purified relatively efficiently due to the turbulent flow created by the non-uniform contour of the germicidal lamp 10. Additionally, if desired, flow over the germicidal lamp 10 may be increased with the use of any conventional fan or blower system 38. The germicidal lamp 10 may be shielded from view by shield 36. Additionally, shield 36 may be shaped so as to enhance the airflow to and over the germicidal lamp 10. The air purification embodiment of the present invention may have particular applicability in health care facilities, such as a hospital.

The present invention provides a germicidal lamp and purification system that may be utilized to increase the efficiency of purification systems. Due to the non-uniform contour of the germicidal lamps, turbulence is created that enhances the exposure of the fluid to the ultraviolet electromagnetic radiation emitted by the germicidal lamp. This enhances the germicidal effectiveness and substantially reduces the required exposure time and size of the purification systems.

Accordingly, while various embodiments have been illustrated and described, it will be obvious to those skilled in the art that various modifications may be made without departing from the spirit and scope of this invention.

What is claimed is:

1. A germicidal lamp for use in a purification system comprising:
   a cylindrical ultraviolet lamp; and
   a transparent envelope having an exterior non-uniform surface contour enclosing said cylindrical ultraviolet lamp, whereby the exterior non-uniform surface contour is capable of creating turbulent flow.

2. A germicidal lamp as in claim 1, wherein:
   the exterior non-uniform surface comprises grooves.

3. A germicidal lamp as in claim 1 wherein:
   the exterior non-uniform surface comprises a helix.

4. A germicidal lamp as in claim 1 wherein:
   the exterior non-uniform surface comprises a double helix.

5. A germicidal lamp as in claim 1 wherein:
   said ultraviolet lamp comprises a fluorescent lamp.

6. A water purification system comprising:
   a chamber for containing a fluid to be purified; and
   an ultraviolet lamp comprising an exterior non-uniform surface contour placed within said chamber so that the fluid to be purified flows over the exterior non-uniform surface contour,
   whereby the exterior non-uniform surface contour is capable of creating turbulent flow.

7. A water purification system comprising:
   a chamber for containing a fluid to be purified;
   an ultraviolet lamp comprising an exterior non-uniform surface contour placed within said chamber, wherein said ultraviolet lamp comprises,
   a cylindrical lamp; and
   a transparent envelope placed over said cylindrical lamp, said transparent envelope having the exterior non-uniform surface contour, said transparent envelope placed within said chamber so that the fluid to be purified flows over the exterior non-uniform surface contour,
   whereby the exterior non-uniform surface contour is capable of creating turbulent flow.

8. A water purification system as in claim 6 wherein:
   the non-uniform surface contour comprises grooves.

9. A water purification system as in claim 6 wherein:
   the non-uniform surface contour comprises a helix.

10. A water purification system as in claim 6 wherein:
    said ultraviolet lamp comprises a fluorescent lamp.

11. An air purification system comprising:
    a room having air therein;
    an ultraviolet lamp having an exterior non-uniform surface contour placed within said room, wherein said ultraviolet lamp comprises,
    a cylindrical lamp; and
    a transparent envelope placed over said cylindrical lamp, said transparent envelope having the exterior non-uniform surface contour,
    whereby the exterior non-uniform surface contour is capable of creating turbulent flow in the air.

12. A method of purifying a fluid comprising the steps of:
    providing fluid having a flow; and
    placing within the fluid flow an ultraviolet lamp comprising an exterior non-uniform surface contour, so that the fluid flows over the exterior non-uniform surface contour,
    whereby the exterior non-uniform surface contour is capable of creating turbulent flow.

13. A fluid purification system comprising:
    a chamber for containing a fluid to be purified;
    a cylindrical ultraviolet lamp,
    a tubular transparent envelope having an exterior non-uniform surface contour placed over said cylindrical ultraviolet lamp, said cylindrical ultraviolet lamp and said tubular transparent envelope placed within said chamber;

at least one end cap placed on said tubular envelope sealing said cylindrical ultraviolet lamp within said tubular transparent envelope wherein the fluid to be purified can not enter between said cylindrical ultraviolet lamp and said tubular transparent envelope so that the fluid to be purified flows over the exterior non-uniform surface contour of said tubular transparent envelope; and electrical connectors extending through said at least one end cap, whereby the exterior non-uniform surface contour is capable of creating turbulent flow by contact with the fluid in said chamber.

14. A fluid purification system as in claim 13 wherein:

the longitudinal axis of said tubular transparent envelope is placed transverse to the flow direction of the fluid.

* * * * *